United States Patent [19]

Senter et al.

[11] Patent Number: 4,625,014

[45] Date of Patent: Nov. 25, 1986

[54] CELL-DELIVERY AGENT

[75] Inventors: Peter D. Senter, Jamaica Plain; John M. Lambert; Walter A. Blattler, both of Brookline, all of Mass.

[73] Assignee: Dana-Farber Cancer Institute, Inc., Boston, Mass.

[21] Appl. No.: 629,363

[22] Filed: Jul. 10, 1984

[51] Int. Cl.[4] .......................... C07K 7/00; A61K 37/02
[52] U.S. Cl. ..................................... 530/300; 530/350; 530/380; 530/387; 530/402; 530/403; 530/808; 530/810; 424/85; 424/88; 435/181; 436/547
[58] Field of Search ............ 260/112.5, 112 R, 112 B; 424/85, 88; 436/547, 905; 435/181

[56] References Cited

U.S. PATENT DOCUMENTS 4,359,457 11/1982 Neville, Jr. et al. .
4,363,758 12/1982 Masuho et al. ........................ 424/85
4,440,747 4/1984 Neville, Jr. et al. ................... 424/85

FOREIGN PATENT DOCUMENTS 0031999 7/1981 European Pat. Off. .............. 424/85
0044167 1/1982 European Pat. Off. .............. 424/85

OTHER PUBLICATIONS

Photochemistry, Colnert et al., ed. John Wiley & Sons, 1966, pp. 477–480.
Method of Enzymology XLIV, Photochemical Immobilization of Enzymes and other Biochemical, Guire, pp. 280–288.
Ritz et al., (1980) Nature 283: 583–585.
Barbieri et al., (1982) Biochem J. 203:55–59.
Ramakrishnan et al., (1984) Cancer Research 44:1398–1404.
Rich et al., (1975) J. Am. Chem. Soc. 97:1575–1579.
Kaplan et al., (1978) Biochemistry 17:1929–1935.
McCray et al., PNAS (USA) vol. 77, 7237–7241 (1980).
Irvin (1983) Pharmac. Ther. 21:371–387.
Barbieri et al., (1982) Cancer Surv. 1:489–520.
Imai et al., (1983) Cancer Imm. 15:206 et seq.
Patchornik et al., (1970) J. Am. Chem. Soc. 92:6335.
Nargeot et al., (1980) PNAS (USA) 80:2395–2399.

Primary Examiner—John Kight
Assistant Examiner—Garnette D. Draper

[57] ABSTRACT

A photo-cleavable compound for delivery and release of a biologically active substance to selected target cells; the compound includes a binding partner for a specific cell-surface receptor of those target cells, the biologically active substance to be delivered, and a photo-cleavable bridge between the binding partner and the biologically active substance. When the compound is exposed to a heterogeneous population of target and non-target cells, it binds selectively to the receptors on the surface of the target cells. Exposing the compound to light of selected wave length cleaves it, yielding the active substance.

28 Claims, 3 Drawing Figures

CELL-DELIVERY AGENT

This invention was made with Government support. The Government has certain rights in this invention.

BACKGROUND OF THE INVENTION

This invention relates to delivering biologically active compounds to cells.

In various situations it is desirable to deliver a biologically active compound through the cell membrane to inner cell structures. For example, drugs or cytotoxins may have little effect if trapped in the medium outside the cell membrane but may be extremely potent once inside the cell.

It is also desirable to deliver such biologically active compounds to selected cells in a heterogeneous cell population. For example, in treating diseased or infected cells such as virus-infected cells or transformed or malignant cells, it is desirable to deliver cytotoxins to the diseased or malignant cells but not to normal cells. One approach disclosed for targeting malignant cells uses an antibody-toxin conjugate. The antibody is specific for malignant cells and delivers the toxin to them. To be effective, such systems should deliver the toxin with high selectivity to the target cells, without unnecessarily reducing the effectiveness of the active substance. These problems are particularly important where the goal is destruction of infected or diseased cells in vivo without harming normal cells.

Ritz et al. (1980) Nature 283:583–585 disclose monoclonal antibody (J5) that is specific for common acute lymphoblastic leukemia antigen.

Barbieri et al. (1982) Biochem J. 203:55–59 disclose purification and partial characterization of an antiviral protein known as pokeweed antiviral protein-S ("PAP-S").

Ramakrishnan et al. (1984) Cancer Research 44:1398–1404 disclose conjugating PAP proteins to anti-Thy 1.1, a monoclonal antibody. The conjugate is used to inhibit protein synthesis selectively in Thy 1.1-positive target leukemia cells. The linker used to form the conjugate is N-succinimidyl-3-(2-pyridyldithio) propionate. When the disulfide bond is cleaved, the free PAP toxin is produced.

Neville et al. U.S. Pat. No. 4,359,457 disclose a conjugate of anti-Thy 1.2 monoclonal antibody and ricin used as a tumor suppressive composition against lymphoma. The linking agent used is m-maleimidobenzoyl-N-hydroxysuccinimide.

The above approaches either depend on the toxicity of an antibody-toxin conjugate, or they depend on disulfide bond cleavage, a phenomenon that may be difficult to control temporally and spatially to avoid release of the toxin before delivery to the targeted cells.

Rich et al. (1975) J. Am. Chem. Soc. 97:1575–9 disclose a 3-nitro-bromomethylbenzoylamide polystyrene resin to immobilize amino acids for solid-phase peptide synthesis. The synthesized peptide is detached from the resin by photolysis.

Patchornik et al. (1970) J. Am. Chem. Soc. 92:6333–6335 disclose the use of o-nitrobenzyl derivatives for protecting the amino function of peptides. The protecting group is removed by irradiation with light of wavelengths longer than 3200 Angstroms. Specific blocking groups disclosed are 6-nitroveratryloxy-carbonyl (NVOC) and 2-nitrobenzyloxycarbonyl (NBOC) groups. 2,2'-Dinitrodiphenylmethanol is disclosed as a blocking group for the carboxylic terminal function of a peptide chain.

Kaplan et al. (1978) Biochemistry 17:1929–1935 disclose inactivated ("caged") adenosine 5'-triphosphate (ATP) that is covalently attached to 2-nitrobenzyl and 1-(2-nitro) phenethyl groups. The caged ATP is exposed to light to release ATP upon demand.

Nargeat et al. (1980) PNAS (USA) 80:2395–2399 disclose U.V. irradiation of o-nitrobenzyl esters of cAMP and cGMP to generate cAMP and cGMP in a biological system.

SUMMARY OF THE INVENTION

One aspect of the invention features a photocleavable compound for delivery and release of a biologically active substance to selected target cells; the compound includes a binding partner for a cell-surface receptor, the biologically active substance, and a photo-cleavable bridge between the binding partner and the biologically active substance. When the compound is exposed to a heterogeneous population of target and non-target cells, it binds selectively to receptors on the surface of the target cells. Exposing the compound to light cleaves it, yielding the active substance.

In preferred embodiments, the biologically active substance is a peptide cytotoxin, and the binding partner is a compound such as a monoclonal antibody that is selective for a cell surface antigen specific to diseased or infected cells, particularly malignant or transformed cells. The term "peptide" is used herein to include proteins as well as shorter chain peptides. Preferably the antibody is one that is taken up by those cells. The bridge is an o-nitrobenzyl function, with the peptide being attached by a cleavable link to the benzylic carbon, and the antibody being attached by a cleavage resistant link to the aromatic ring.

In one particularly preferred embodiment, the photocleavable compound has the following formula:

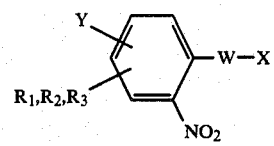

where W comprises an oxycarbonyl function, an aminocarbonyl function, or a phosphate function; one of X and Y comprises a peptide; the other of X and Y comprises a cell-surface binding partner that is either an antibody to a cell-surface antigen or a binding partner for a cell-surface receptor; and each of $R_1$, $R_2$, and $R_3$ is independently selected from —H, a lower alkyl group, a lower alkoxy group, or a cyclic alkyl or aryl group. By the term "lower" alkyl or alkoxy as used in this application, we means $C_5$ or less.

In that embodiment, W is most preferably an oxycarbonyl function, for example, in which the benzylic carbon is covalently bound to the oxy function and to a function "Z" which is —H lower alkyl (most preferably —$CH_3$), cyclic alkyl, or aryl, as in the following formula:

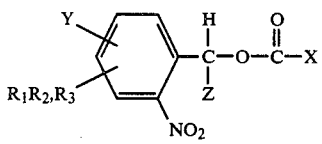

One possible compound where W is an aminocarbonyl function has the formula:

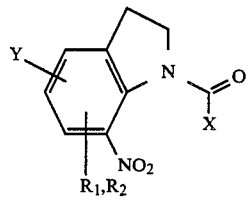

The above-described compounds have significant advantages for tumor control and other cancer therapy where the cell system is accessible to light. So long as the compound is protected from U.V. light, the compound is not cleaved, and normal cells are safe from the effects of the toxin. Linkages in the compound, such as the antibody-bridge link, are designed so that, in the absence of light, they are cleavage resistant to avoid undesired cleavage of the compound that might release a substance with toxic activity.

The photo-cleavage system allows rapid, nearly quantitative release of the active substance at the particular time when, and the particular place where, the compound is illuminated. For example, where the binding partner is an antibody that is taken up by the cells, illumination causes release of the active substance after the above-described compound has been taken up by the cells. The light does not affect the active substance. Light energy required for cleavage is comparable to that currently used for treatment of skin disorders. See, for example, Morrison, W. L. (1983) *Phototherapy and Photochemotherapy of Skin Disease* (Praeger, Publ.).

A second aspect of the invention features generally a method of synthesizing a photo-cleavable compound as described above having an o-nitrobenzyl bridge component. The biologically active substance is a peptide that is linked to the bridge by reacting a peptide nitrogen with an o-nitro-benzyloxycarbonyl-chloride. In preferred embodiments of the method of synthesis, an antibody is functionalized with a maleimido group and linked to the benzyl ring via a sulfide-maleimido linkage. The above synthesis enables a cleavage resistant attachment of the antibody under conditions which do not affect the previously formed bond between the peptide and the o-nitrobenzyl function.

DESCRIPTION OF THE PREFERRED EMBODIMENT

The following is a description of particularly preferred embodiments of the invention, including drawings thereof.

DRAWINGS

STRUCTURE OF THE COMPOUND

Figure 1:
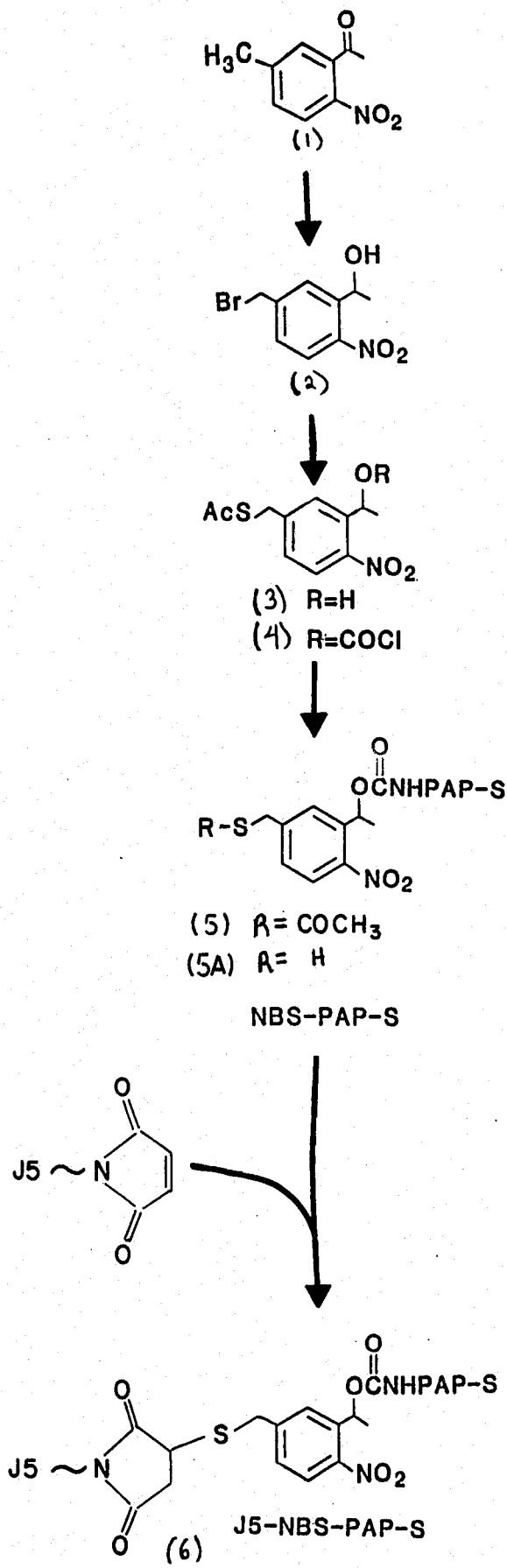
FIG. 1 is a flow diagram for synthesis of J5-NBS-PAP-S (6), where J5 is an antibody, NBS is a nitrobenzylsulfide bridge, and PAP-S is a cytotoxic protein as described below.

In a preferred embodiment, the claimed photocleavable compound has three components: (1) a biologically active substance that is to be delivered into a target cell population; (2) a binding partner for a cell-surface receptor that is specific for the target cells; and (3) a photo-cleavable bridge which includes a covalent linker to the binding partner and a covalent linker to the biologically active substance.

The preferred biologically active substances are cytotoxins, particularly peptide cytotoxins such as the pokeweed antiviral proteins PAP, PAP II, and PAP-S, described above and in Irvin (1983) Pharmac. Ther. 21:371–387. Other peptide cytotoxins include ricin A-chain, abrin A-chain, modeccin A-chain as well as gelonin and other single-chain ribosomal inactivating proteins such as those described in Barbieri et al. (1982) Cancer Surv. 1:489–520.

Peptide toxins are preferred because they are readily linked to the bridge, and because they are extremely potent toxins which inhibit cell protein synthesis when present inside the cell in extremely minute quantities. Other cytotoxins which are not peptides are also within the scope of the invention however; examples of such cytotoxins or cytotoxic drugs are chlorambucil, methotrexate, aminopterin, and melphalan.

The preferred binding partners for the compounds are monoclonal antibodies to cell surface antigens. Particularly preferred are monoclonal antibodies to cell surface antigens specific to diseased, infected, transformed or malignant, but not to normal cells. Particularly, but not exclusively they are antibodies that are taken up by the cells. It is not necessary that normal cells lack the specific antigen entirely, as long as the antigen is not present in sufficient numbers on those cells to permit significant uptake of the active substance by the cells. One such antibody is J5, described above, available from Coulter Immunology, Hialeah Fla. Other examples are antibodies to melanoma surface antigens such as those described by Imai et al. (1983) Cancer Imm. 15:206 et seq. Other suitable antibodies available from Coulter Immunology include the antibodies to surface antigens found on T-cells and T-cell lymphomas such as T3, T4, T11, and T12.

Other binding partners that are within the scope of the invention include non-antibody cell memorane transport agents such as transferrin and protein hormones such as insulin.

The preferred bridge may be thought of as an o-nitrobenzyl function with two linking entities, one to the active substance and the other to the cell binding partner. Substituents on ring sites not occupied by linkers may be selected, independently, from -H, a lower alkyl or alkoxy group or a cyclic alkyl or aryl group. Preferably, the photo-cleavable site is at the site of attachment between the toxin and its linker so that the naturally-occurring toxin is released without artifacts of the photo-cleavable compound attached to it.

One particularly preferred photo-cleavable linker is the o-nitrobenzyloxycarbonyl function with a methyl group optionally attached to the benzylic carbon. In place of the oxycarbonyl function, a phosphate or thiocarbonyl function may be used. Finally, the above-described 7-nitroindolinyl-amide function may be used to photo-cleavably link the active substance to the cell binding partner. Where the active substance is a peptide, it is preferably linked to the carbonyl carbon of the oxycarbonyl function via an amino nitrogen.

The link between the bridge and the cell binding partner is also important, because if that link is cleaved by natural processes (e.g., by enzymes in an in vivo system) at an undesired time or place, the selectivity of the binding partner is lost, and the toxin, or a compound with potential toxic activity, is present in the medium outside the cells without a means for selecting the target cells.

One suitable cleavage resistant link is a thioether link formed between a sulfhydryl group and a maleimido function that has been added to the antibody. See the structure of J5-NBS-PAP-S (6) below. Another less preferred cleavage resistant link is between a maleimido function on an antibody and a sulfhydryl group of a mercapto propanoate ester. See the structure of J5-NBE-PAP-S (10) below. The cell binding partner is preferably linked to the ring meta or para to the $-NO_2$ function, and that link comprises a sulfide bound to a maleimido group of a functionalized antibody.

Synthesis of the Compound

In general, the preferred compounds are synthesized by condensing the peptide with a function on the benzylic carbon of an o-nitrobenzyl ring. A protected sulfhydryl group which will later be used to form the antibody link has been introduced onto the ring previously.

For example, if the peptide is to be linked by an oxycarbonyl function, an oxycarbonyl chloride or an oxycarbonyl imidazole may be condensed with an amino function of the peptide. The oxycarbonyl chloride and oxycarbonyl imidazole are synthesized from the corresponding alcohol using phosgene and carbonyldiimidazole, respectively.

If the linker is a phosphate function, the corresponding o-nitrobenzyl alcohol is reacted with phosphorusoxychloride to yield a dichlorophosphate ester which is condensed with the peptide. Alternatively, the alcohol is condensed with dichloroethylphosphate to yield a chloroethyl phosphate that is condensed with the peptide.

The covalent linkage between the antibody and the o-nitrobenzyl function is achieved by attaching a sulfhydryl group to the ring, protecting it during the above-described peptide linkage, and then reacting the deprotected sulfhydryl group with a maleimide functionalized antibody.

The following descriptions of the details of synthesis of two specific cell-delivery compounds illustrate the above synthetic scheme. The two compounds are both conjugates of the monoclonal antibody J5 described above, and the toxin PAP-S, also described above, using somewhat different o-nitrobenzyzl linker functions. For convenience, the two compounds are designated J5-NBS (for nitrobenzylsulfide)-PAP-S (6) and J5-NBE (for nitrobenzylester)-PAP-S (10).

I. Synthesis of J5-NBS-PAP-S (6)

FIG. 1 illustrates the synthesis of an antibody-protein toxin conjugate designated as J5-NBS-PAP-S. The numbers used in parentheses in the following description refer to the numbers assigned to intermediate and product compounds diagrammed in FIG. 1.

A. Synthesis of 1-(5-Bromomethyl-2-nitrophenyl)-ethanol (2)

Compound 2 is synthesized in two steps from 1-(5-methyl-2-nitrophenyl) ethanone (1), which can be obtained as described by Doppler et al. (1979) Helv. Chem. Acta 62:291–303. Specifically, the ring methyl group is brominated using N-bromosuccinimide and then the benzylic ketone is reduced to an alcohol. Those procedures are described below.

A mixture of 20.0 g (0.111 mol) of 1-(5-methyl-2-nitrophenyl) ethanone, 21.85 g (0.123 mol) of N-bromosuccinimide and 269 mg (1.11 mmol) of benzoylperoxide in 100 mL of $CCl_4$ is heated at reflux under $N_2$ for 4 h. At this stage, the succinimide produced in the reaction floats on top of the yellow solution. The mixture is cooled, filtered, and the filtrate is evaporated to dryness. A solution of the residue in $CH_2Cl_2$ is washed with water and then dried ($MgSO_4$). Evaporation of the solvent furnishes a yellow solid. Recrystallization from ether provides the bromide as fine white needles. The resulting brominated compound, 1-(5-Bromomethyl-2-nitrophenyl)-ethanone, can be identified by the following characteristics: mp 77°–78°. IR ($CHCl_3$) νmax 1720 (C=0), 1350 ($NO_2$); $^1H$ NMR ($CDCl_3$) δ2.53 (s, 3H, $CH_3$), 4.46 (s, 2H, $CH_2Br$), 7.2–8.2 (m, 3H, ArH).

Compound 2 is then prepared by adding 360 mg (9.47 mmol) of $NaBH_4$ over a five minute period to an ice cold solution of 5 g (19.4 mmol) of 4-(5-bromomethyl-2-nitrophenyl)-ethanone in 25 mL of dioxane and 35 mL of methanol. After 10 min, the mixture is warmed to room temperature and stirred 10 min. Any remaining reductant is quenched with acetone, and the solvent is evaporated. A solution of the residue in $CHCl_3$ is washed with saturated aqueous NaCl and then dried ($MgSO_4$). The solution is thus concentrated to a viscous yellow oil of (2) which solidifies upon standing.

Compound 2 has the following characteristics: mp 36°–39°. IR (film) νmax 3400 (OH), 1525 ($NO_2$), 1350 ($NO_2$) $^1H$ NMR ($CDCl_3$) δ1.60 (d, J=7 Hz, 3H, $CHCH_3$), 4.45 (s, 2H, $CH_2Br$), 5.45 (q, J=7 Hz, 1H, $\underline{CH}CH_3$), 7.2–8.0 (m, 3H, ArH).

B. Synthesis of [4-Nitro-3-(1-hydroxyethyl) phenyl] methyl-3-S-acetylthioic Acid Ester (3).

Compound 3 is prepared from the above-described compound 2 by replacing the bromine with an acetylthioic acid ester function as follows.

A solution of 0.35 mL (5 mmol) of thioacetic acid in 5 mL of DMF is stirred at room temperature while 3.28 mL (5 mmol) of a 40% aq. solution of tetrabutylammonium hydroxide is slowly added. To this is added 1.00 g (3.85 mmol) of the benzyl bromide (2) in 5mL of DMF and stirring is continued for 30 min. The solvent is evaporated and a solution of the residue in ether is extracted with satd. aq. NaCl, dried ($MgSO_4$) and evaporated. Purification of the residue by flash chromatography on a 3×20 cm $SiO_2$ column with 40% ether in petroleum ether as eluant provides 0.534 g (54%) of (3) as a viscous yellow oil.

Compound 3 has the following characteristics: IR (film) νmax 3400 (OH), 1680 (C=0), 1515 ($NO_2$), 1340 ($NO_2$), $^1H$ NMR ($CDCl_3$) δ1.55 (d, J=6 Hz, 3H, $CH\underline{H}_3$), 2.33 (s, 3H, $COCH_3$), 2.5 (br.s, 1H, OH), 4.13 (s, 2H, $ArCH_2$), 5.4 (q, J=6 Hz, 1 Hz, 1H, $\underline{CH}CH_3$), 7.2–8.0 (m, 3H, ArH).

C. Conversion of Benzyl Alcohol (3) to Benzyloxycarbonyl Chloride (4). Compound 3 is converted to the corresponding benzyloxycarbonyl chloride (4) using trichloromethylchloroformate (diphosgene) as follows.

To a solution of 225 (mg 0.88 mmol) of (3) in 4 mL of dry dioxane is added 71 µL (0.88 mmol) of pyridine followed by 105 µL (0.88 mmol) of trichloromethylchloroformate (diphosgene). A precipitate is immediately deposited. The reaction is followed by TLC using 50% ethyl acetate in petroleum ether as eluant and is complete in 1 h. The dioxane is evaporated and high vacuum is applied to the residue for 1 h to remove any remaining diphosgene. A mixture of the product in 50% ether in petroleum ether is filtered through Celite and evaporation of the solvent gives (4) as a yellow oil.

Compound 4 has the following characteristics: IR (film) $\nu$max 1775 (C=O, chloroformate), 1680 (C=O S-acetate), 1525 ($NO_2$), 1350 ($NO_2$). $^1$H NMR (CDCl$_3$) $\delta$1.90 (d, J=6 Hz, 3H, CHC$\underline{H}_3$), 2.45 (s, 3H, COC$\underline{H}_3$), 4.2 (s, 2H, ArCH$_2$S), 6.4 (q, $\overline{J}$=6 Hz, 1H, ArC$\underline{H}$CH$_3$), 7.2–8.2 (m, 3H, ArH).

D. Preparation of NBS-PAP-S (5)

Isolation of PAP-S from the seeds of *Phytolacca americana* is described by Barbieri et al., cited above. PAP-S is reacted with the benzyloxycarbonyl chloride function of compound 4 to yield NBS-PAP-S as follows.

A solution of 0.01 M benzyloxycarbonyl chloride 4 (20 µL, 0.2 µmol) in dry dioxane is added to a solution of PAP-S (4 mg, 0.13 µmol) in 100 mM aq. NaHCO$_3$ (4 mL) at pH 8.3. After 35 min. at room temperature, the sample was centrifuged to remove small amounts of precipitate formed. The supernatant is purified by gel filtration on a Sephadex G-25 (fine) column equilibrated with phosphate buffered saline (PBS) containing 1 mM EDTA. Phosphate buffered saline (PBS) refers to 10 mM potassium phosphate and 145 mM NaCl at pH 7.2. The degree of protein modification is determined by aminolysis of a sample (1.2 mL) with 0.5 M hydroxylamine, pH 7.3 (0.12 mL) for 35 min. at room temperature by the method of Liu et al., (1979) Biochemistry 18:690–697, the amount of liberated thiol being estimated by reaction with 5,5'-dithio-bis(2-nitrobenzoic acid) [DTNB, see Ellman, (1959) Arch. Biochem. Biophys. 82:70–77]. The analysis indicates that the PAP-S contained an average of 0.61 nitrobenzyl groups per protein molecule. The protein concentration is determined from the absorbance at 280 nm ($E_{1\ cm}^{1.0\%}$ =0.88) after correction for the absorbance due to the nitrobenzyl group ($\epsilon_{280}$ in H$_2$O=6810).

E. Preparation of J5-NBS-PAP-S (6)

Monoclonal antibody J5 is prepared as described by Ritz et al., 1980 cited above, and is purified by affinity chromatography on protein A sepharose 4B-CL as described by Ey, et al., (1978) Immunochemistry 15:429–436, followed by cation exchange chromatography on carboxymethyl cellulose. J5 functionalized with maleimido groups, as described in II. D., below, is then conjugated to compound (5) as follows.

To a solution of 5.74 mg of NBS-PAP-S (5) (0.85 nitrobenzyl groups/protein molecule) in 1.49 mL of PBS is added 0.15 mL of a 0.5 M hydroxylamine solution at pH 7.3 containing 1 mM EDTA. After 30 min. at room temperature, the solution is applied to a Sephadex G-25 (fine) column equilibrated with 100 mM potassium phosphate containing 0.5 mM EDTA at pH 7.0 The modified NBS-PAP-S (5a), which now contains free sulfhydryl groups, is added to maleimido-functionalized J5 antibody (5.74 mg) and kept at 4° C. overnight. Purification of the conjugate is the same as described below for J5-NBE-PAP-S (10). Polyacrylamide-SDS gel electrophoresis indicates that the purified conjugate consists mainly of 1:1 J5-PAP-S (66%) adducts with small amounts of higher molecular weight adducts, and free J5 antibody (9%).

II. Preparation of J5-NBE-PAP-S (10)

Figure 2:
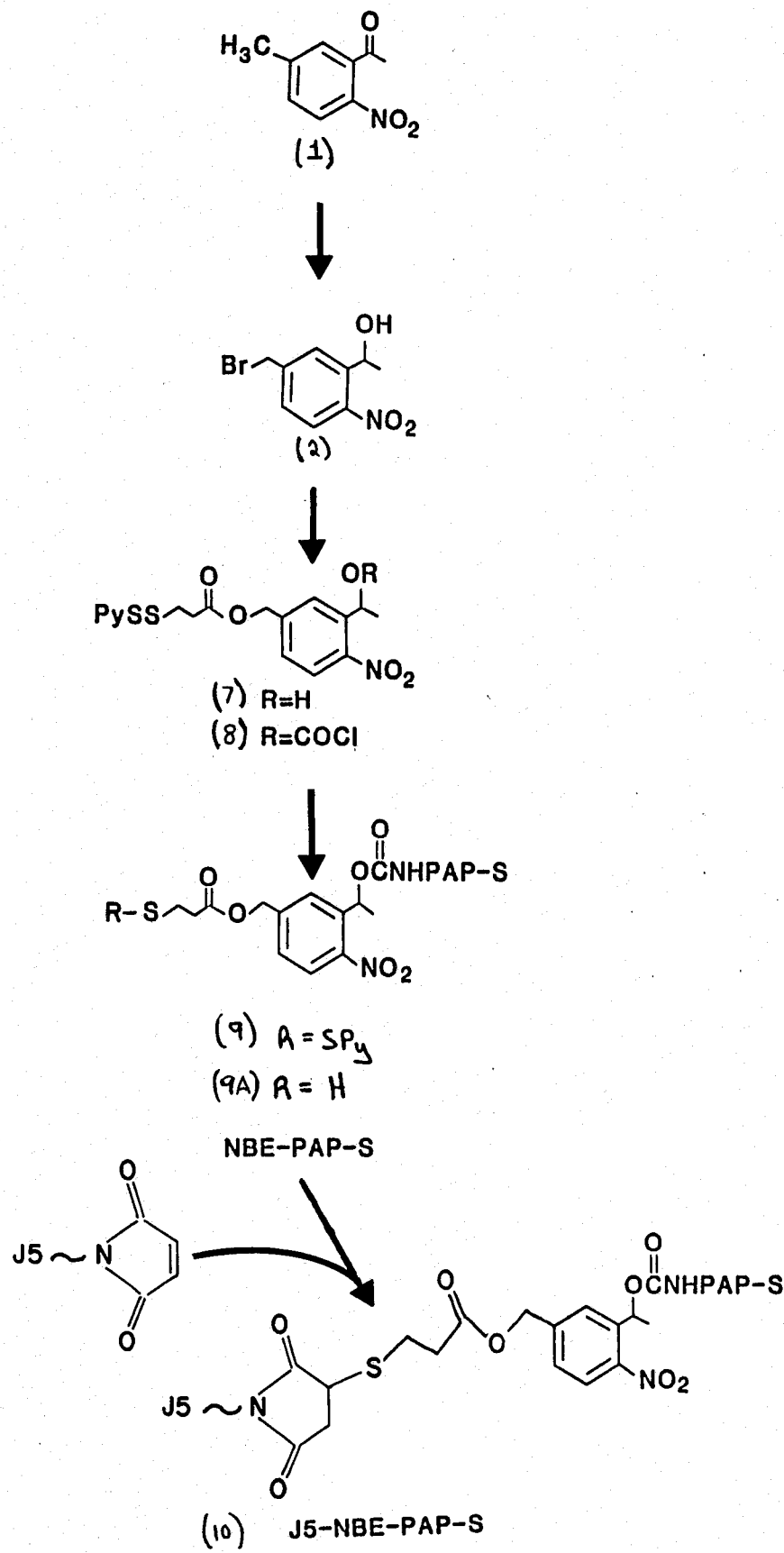
FIG. 2 is a flow diagram for synthesis of J5-NBE-PAP-S (10), where the terms have the meanings prescribed above, and NBE is a nitrobenzylester bridge.

FIG. 2 illustrates the steps in the synthesis of J5-NBE-PAP-S (10). Compounds 6 and 10 differ only in the means for linking J5 to the nitrobenzyl entity.

A. Synthesis of [4-Nitro-3-(1-hydroxyethyl) phenyl] methyl-3-(2-pyridyldithiopropanoic acid) Ester (7).

Compound 7 is synthesized from 1-(5-Bromomethyl-2-nitrophenyl)-ethanol (2) (see I. A., above) by replacing the ring bromine with a pyridyldithiopropanoate group as follows.

A solution of 1.07 g (4.99 mmol) of pyridyldithiopropanoic acid in 5 mL of DMF is stirred at room temperature while 3.24 mL (4.99 mmol) of 40% aq. tetrabutylammonium hydroxide is slowly added. To the solution of the resulting colorless carboxylate salt is added 1.0 g (3.84 mmol) of (2) in 5 mL of DMF and stirring is continued for 2 h. The solvent is evaporated, and a solution of the residue in CH$_2$Cl$_2$ is washed successively with water, satd. aq. NaCl. The solution is dried over MgSO$_4$ and evaporated. Purification of the residue by flash chromatography on a 3×26 cm column with 40% ethyl acetate in petroleum ether provides (7) as a viscous yellow oil.

The characteristics of (7) are as follows: IR (film) $\nu$max 3300 (OH), 1740 (C=O), 1520 ($NO_2$), 1420 ($NO_2$), $^1$H NMR (CDCl$_3$) $\delta$1.55 (d, J=6 Hz, 3H, CHC$\underline{H}_3$), 2.8–3.3 (m, 4H, CH$_2$CH$_2$), 5.13 (s, 2H, ArC$\underline{H}_2$), 5.5 (q, J=6 Hz, 1H, C$\underline{H}$CH$_3$), 6.9–7.9 (m, 6H, ArH), 3.8–8.5 (m, 1H, ArH).

B. Conversion of Benzyl Alcohol (7) to Benzyloxycarbonyl Chloride (8) Benzyl alcohol (7) is converted to the corresponding benzyloxycarbonyl choride (8) by exposure to diphosgene (see I. C., above), as follows.

To a solution of 100 mg (0.254 mmol) of 7 in 1.02 mL of dry dioxane is added 30.5 µL (0.254 mmol) of diphosgene. After 20 hr at room temperature, the solvent is evaporated and high vacuum is applied to the residue for 30 min. The resulting hydrochloride salt of 10 is finely dispersed in 10 mL of anhydrous dioxane by sonication and is used in the preparation of NBE-PAP-S (9) without further purification.

To analyze compound 8, an analytical sample of the free base is obtained by the addition of excess N-ethylmorpholine to a dioxane suspension of the hydrochloride salt. The mixture is stirred for 10 min., and the solvent is evaporated under high vacuum. A suspension of the product in ether is filtered through Celite and the filtrate is concentrated to a yellow oil. The characteristics of the resulting free base are: IR (CDCl$_3$) $\nu$max 1740 (C=O), 1530 ($NO_2$), 1420 ($NO_2$). $^1$H NMR (CDCl$_3$) $\delta$1.60 (d, J=6 Hz, 3H, CHC$\underline{H}_3$), 2.6–3.1 (m, 4H, CH$_2$CH$_2$), 5.10 (s, 2H, ArCH$_2$), 6.10 (q, J=6 Hz, 1H, C$\underline{H}$CH$_3$), 6.9–8.4 (m, 7H, ArH).

C. Preparation of NBE-PAP-S (9)

PAP-S prepared as described in I. D., above is conjugated to compound (8) as follows.

A solution of 25.4 mM benzyloxycarbonyl chloride (8) (0.4 mL, 10.2 μmol) in dry dioxane is added to a solution of PAP-S (12 mg, 0.4 μmol) in 100 mM aq. NaHCO$_3$ (12 mL) at pH 8.3. After 30 min at room temperature, the precipitate is removed by centrifugation. The supernatant is purified by gel filtration on a Sephadex G-100 column eouilibrated with PBS containing 1 mM EDTA. The degree of protein modification is determined by reduction with dithioerythritol and measurement of the thiopyridine released, see Carlsson et al. (1978) Biochem J. 173:723–737. This analysis indicates the average of nitrobenzyl groups that the protein contains is about 0.60 per protein molecule. The protein concentration is determined from the absorbance at 280 nm after correction for the absorbance due to the nitrobenzyl ester ($\epsilon_{280}=8890$).

D. Preparation of J5-NBE-PAP-S (10)

Compound 14 is conjugated to J5 monoclonal antibody (see I.E., above) as follows.

To a solution of 7.59 mg of J5 in 7.59 mL of 100 mM potassium phosphate and 0.5 mM EDTA at pH 7 at 30° C. is added 41.5 μL of a 10 mM succinimidyl-4-(N-maleimidomethyl)-cyclohexane-1-carboxylate (SMCC, Pierce Chemical Co.) in dioxane After 30 min. at 30°, the antibody is separated from excess reagent by gel filtration through a column of Sephadex G-25 (fine) equilibrated with the above buffer. The modified antibody, which elutes in a volume of 15 mL, is treated with NBE-PAP-S modified as described below.

An excess of dithioerythritol is added to a solution of 5.74 mg of NBE-PAP-S (9) (0.60 nitrobenzyl groups/protein molecule) in 3.7 ml of PBS containing 1 mM EDTA. After 15 min. at room temperature, the excess reductant is removed by gel filtration on Sephadex G-25 (fine) equilibrated with 100 mM potassium phosphate and 0.5 mM EDTA at pH 7. The product (9a) is added to maleimido-functionalized J5 antibody and kept at 4° C. overnight.

The reaction mixture is applied to a 3 mL Protein A-Sepharose column as described by Ey et al., (1978) Immunochemistry supra and washed with PBS. Antibody and antibody-containing conjugates are bound by the protein A and are eluted with 0.1 M acetic acid containing 0.15 M NaCl. The protein mixture is dialyzed against 5 mM potassium phosphate containing 35 mM NaCl at pH 6.5 and applied to a 3 mL CM-cellulose column equilibrated with the same buffer. Unconjugated antibody is not bound by CM-cellulose under these conditions. The column is washed with 150 mL of buffer, and the conjugate is eluted with 5 mM potassium phosphate and 0.5 M NaCl at pH 6.5 and dialyzed against PBS. Polyacrylamide-SDS gel electrophoresis is used to establish the composition of the conjugate in terms of J5-PAP-S adducts, free J5 antibody, and higher molecular weight adducts.

Photo-Cleavage and Use

Figure 3:
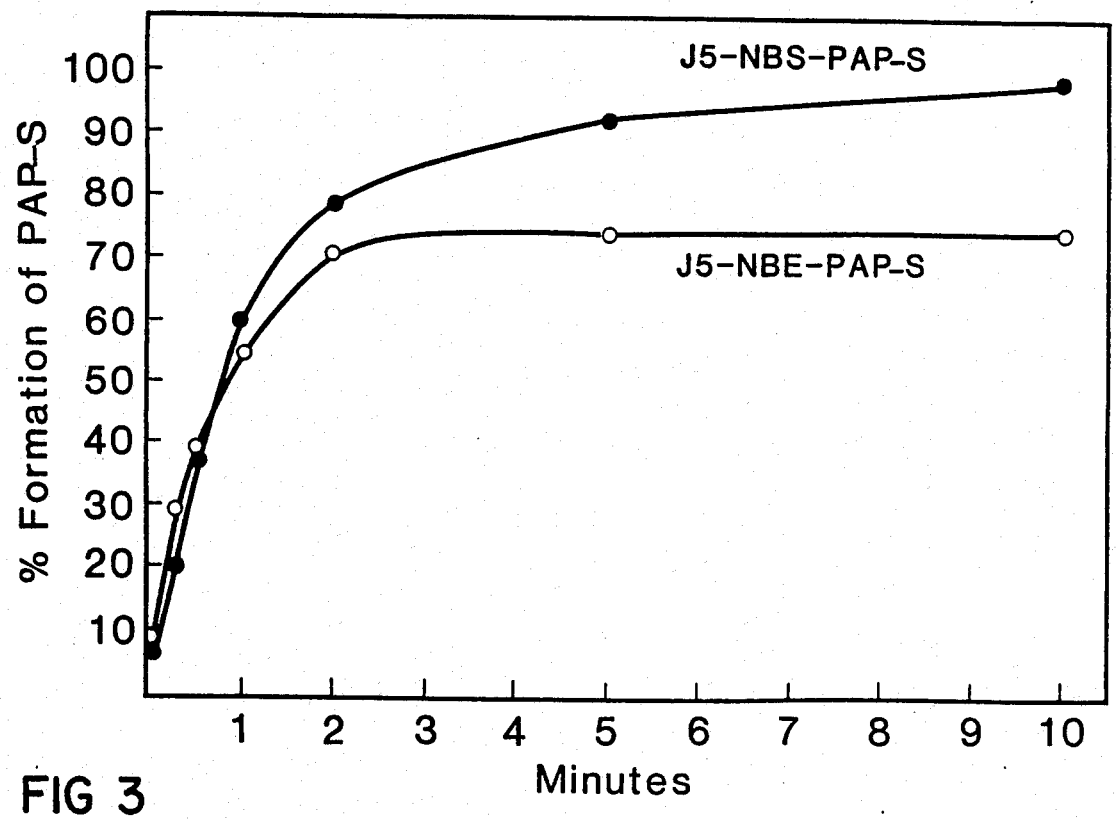
FIG. 3 is a graph of appearance of PAP-S as a function of time of irradiation of J5-NBS-PAP-S (6) and J5-NBE-PAP-S (10).

Photo-cleavage of the compounds can be demonstrated by exposing them to a low energy U.V. light (e.g. peak intensity about 365 nm), and measuring the rates of appearance of the toxin and antibody using polyacrylamide-SDS gel electrophoresis. For J5-NBS-PAP-S (6) and J5-NBE-PAP-S (10), samples contained in a 96-well polystyrene tissue culture plate are irradiated at a distance of 15 cm from a Blak Ray Longwave Ultraviolet Lamp (Model B-100A, Ultraviolet Products, Inc., San Gabriel, Calif.). Portions (10 μL) are removed and the proteins are denatured by the addition of a solution (10 μL) of 5% (w/v) SDS in 0.125 M Tris-HCl buffer, pH 6.8, containing glycerol (10% v/v), iodoacetamide (10 mM) and bromophenol blue. After heating for 2 min at 90°, the samples are applied to a 5–12% polyacrylamide-SDS gradient gel and submitted to electrophoresis. The gel is stained with Coomassie blue and the band intensities are quantified with a Helena Laboratories gel scanner. FIG. 3 depicts the % formation of PAP-S compared to the theoretical possible yield over time. Most of the PAP-S is released within two minutes of the onset of exposure to light.

The toxicity of the released toxin aliquot is measured and verifies that the chemical modification and cleavage do not alter the activity of the toxin A cell-free assay of protein synthesis is satisfactory for this purpose for toxins such as PAP-S. Assays of cell-free protein synthesis are performed using a rabbit reticulocyte lysate system purchased from New England Nuclear Corp., Massachusetts.

The compounds are generally useful for delivering biologically active substances to target cells in a heterogeneous cell population. For example, when engineering cells for industrial purposes it may be useful to selectively treat cells having specific desired or undesired characteristics by introducing toxins or nutrients to those cells selectively.

Medically, the compounds are useful for in vivo tumor suppression because an active, unmodified form of the toxin is selectively delivered only to malignant cells. The treatment is useful for any diseased or infected cells, e.g. cancer cells, that are light accessible such as skin cancers, blood diseases (by circulating the blood cells outside of the patient) or other cells such as bone marrow cells which can be removed from and replaced in a patient.

The light used to cleave the compound should be of sufficient energy to cause rapid, effectively quantitative cleavage without affecting the toxin entity. For o-nitrobenzyl functions generally, a peak wavelength of between 250 and 380 nm and most preferably between 350 and 380 nm may be used. The light must also be chosen to be free from interference from other absorbing substances in the system such as hemoglobin.

Irradiation should be performed for a period long enough to generate maximal release of the active substance and short enough to avoid harming the cells. The time of irradiation should generally be from 2-10 minutes (see FIG. 3) for the preferred system but may vary depending on the light source's peak wavelength and wavelength distribution as well as the peak intensity and the cell line susceptibility. Filters may be used to truncate undesired wavelengths.

Other Embodiments

Other embodiments are within the following claims. For example, other o-nitrobenzyl functions may be used in place of the functions described in the preferred embodiment. Methoxy functions or other electron withdrawing functions may be substituted at one or more locations on the nitrobenzyl ring. Photocleavable 7-nitroindolines may be used as the photocleavable bridge. These compounds and their preparation are described by Amit et al. (1976) J. Am. Chem. Soc.

98:843 et seq. The photo-cleavage properties of a proposed bridge may be tested using an organic function whose appearance is easily followed in place of the peptide. For example a 2-ethylbutyric acid function or a benzylamine function may be used.

Other antibodies, e.g. those which are not themselves transported across the cell membrane, may be used in conjunction with an active substance that is self-transporting in its free form, but not when conjugated to the antibody.

What is claimed is:

1. A photocleavable compound having the formula,

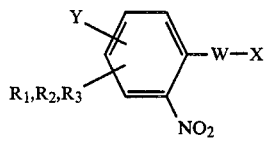

where W comprises an oxycarbonyl function, an aminocarbonyl function, or a phosphate function; one of X and Y comprises a peptide; the other of X and Y comprises a cell-surface binding partner that is either an antibody to a cell-surface antigen or a binding partner for a cell-surface receptor; and each of $R_1$, $R_2$, and $R_3$ is independently selected from —H, a lower alkyl group, a lower alkoxy group, or a cyclic alkyl or aryl group.

2. The compound of claim 1 wherein said peptide is cytotoxic.
3. The compound of claim 2 wherein said cytotoxic peptide is a protein synthesis inhibitor.
4. The compound of claim 3 wherein said cytotoxic peptide is a ribosomal inactivating protein.
5. The compound of claim 4 wherein said cytotoxic peptide comprises a pokeweed antiviral protein, gelonin, the ricin A-chain, abrin A-chain, or modeccin A-chain.
6. The compound of claim 1 wherein X comprises said peptide and Y comprises said cell-surface binding partner.
7. The compound of claim 1 wherein said cell-surface binding partner comprises an antibody to a cell-surface antigen.
8. The compound of claim 1 wherein said cell-surface binding partner is transferrin.
9. The compound of claim 1 wherein said cell-surface binding partner is a peptide hormone.
10. The compound of claim 9 wherein said hormone is insulin.
11. The compound of claim 1 wherein W comprises an oxycarbonyl function.
12. The compound of claim 11 having the following formula,

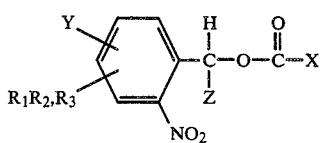

wherein X, Y, $R_1$, $R_2$, and $R_3$ are defined as in claim 11, and Z is —H, lower alkyl, cyclic alkyl, or aryl.

13. The compound of claim 11 or 12 wherein the carbonyl group of said oxycarbonyl function is bonded to the nitrogen of an amino group of said peptide.

14. The compound of claim 1 wherein W comprises an aminocarbonyl function.
15. The compound of claim 14 having the following formula,

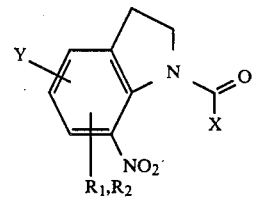

wherein X, Y, $R_1$, and $R_2$ are as defined in claim 14.

16. The compound of claim 7 wherein Y is meta or para to the nitrate group and Y comprises a cleavage resistant sulfide bond.
17. The compound of claim 16 wherein said sulfide is bound to a maleimido function, and maleimido function being bound to an antibody.
18. The compound of claim 7 wherein said cell binding partner is an antibody to a T-cell surface antigen.
19. The compound of claim 18 wherein said T-cell surface antigen is T3, T4, T11, or T12.
20. The compound of claim 7 wherein said cell binding partner is an antibody to a malanoma surface antigen.
21. The compound of claim 7 wherein said cell binding partner is J5 antibody.
22. The compound of claim 7 or claim 21 having one of the following formulas:

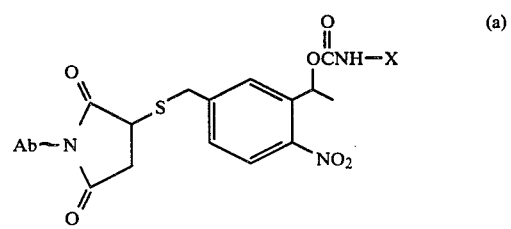

or

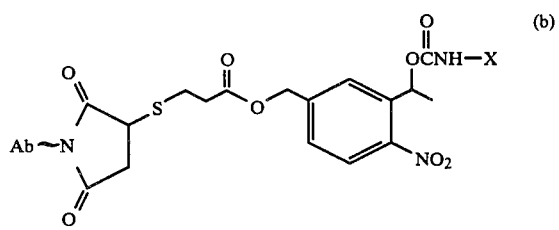

23. The compound of claim 22 wherein X is pokeweed antiviral protein-S.
24. The compound of claim 7 wherein said antibody is an antibody that is transported across cell membranes containing said antigen.
25. A photocleavable compound having the formula,

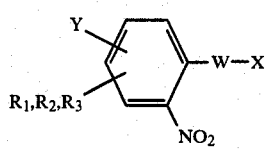

where W comprises an oxycarbonyl function, an aminocarbonyl function, or a phosphate function, one of X and Y comprises a cytotoxin selected from chlorambucil, methotrexate, aminopterin, and melphalan; the other of X and Y comprises a cell-surface binding partner that is either an antibody to a cell-surface antigen or a binding partner for a cell-surface receptor; and each of $R_1$, $R_2$, and $R_3$ is independently selected from —H, a lower alkyl group, a lower alkoxy group, or a cyclic alkyl or aryl group.

26. A method of making the compound of claim 13 comprising
   first reacting an o-nitrobenzyl alcohol with an activating agent to form an activated o-nitrobenzyl oxycarbonyl function, and thereafter
   reacting said activated oxycarbonyl function with said peptide.

27. The method of claim 26 wherein said activated oxycarbonyl function is an oxycarbonyl chloride or an oxycarbonyl-imidazole.

28. The method of claim 26 wherein said o-nitrobenzyl function comprises a protected sulfhydryl function on a chain attached to the nitrobenzyl ring meta or para to the —$NO_2$ function, and
   after said peptide reaction, said protected sulfhydryl function is deprotected and then reacted with a maleimido-functionalized antibody to attach said sulfhydryl group covalently to said maleimido function.

* * * * *